US012138028B2

United States Patent
Ito

(10) Patent No.: US 12,138,028 B2
(45) Date of Patent: Nov. 12, 2024

(54) FLUID ANALYSIS APPARATUS, FLUID ANALYSIS METHOD, AND FLUID ANALYSIS PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 242 days.

(21) Appl. No.: 17/735,097

(22) Filed: May 2, 2022

(65) Prior Publication Data

US 2022/0265156 A1 Aug. 25, 2022

Related U.S. Application Data

(63) Continuation of application No. PCT/JP2020/042058, filed on Nov. 11, 2020.

(30) Foreign Application Priority Data

Dec. 25, 2019 (JP) ................. 2019-235138

(51) Int. Cl.
*A61B 5/026* (2006.01)
*A61B 5/00* (2006.01)
(Continued)

(52) U.S. Cl.
CPC ........... *A61B 5/0263* (2013.01); *A61B 5/055* (2013.01); *A61B 5/742* (2013.01); *G06T 7/0012* (2013.01); *G06T 7/223* (2017.01); *A61B 2576/00* (2013.01); *G06T 2207/10088* (2013.01); *G06T 2207/30104* (2013.01)

(58) Field of Classification Search
CPC . A61B 8/06; A61B 6/507; A61B 2576/00–02; A61B 5/055; A61B 5/0263; G06T 2207/10072–10136; G06T 7/0012–0016; G06T 7/223–238
See application file for complete search history.

(56) References Cited

U.S. PATENT DOCUMENTS 6,741,880 B1  5/2004  Foo et al.
9,724,164 B2  8/2017  Yagi et al.
(Continued)

FOREIGN PATENT DOCUMENTS

JP    H0833625      2/1996
JP    2002095648    4/2002
(Continued)

OTHER PUBLICATIONS

Machine translation of Asanori (JP H0833625 A, Feb. 6, 1996).*
(Continued)

*Primary Examiner* — Carolyn A Pehlke
(74) *Attorney, Agent, or Firm* — JCIPRNET

(57) ABSTRACT

A processor analyzes an image obtained by imaging a subject including a tubular structure in which a fluid flows, thereby deriving fluid information regarding flow of the fluid at each of pixel positions in the tubular structure. The processor sets a sampling interval for displaying the fluid information in accordance with a size of a region intersecting a center line of the tubular structure included in the image. The processor samples the fluid information at the set sampling interval and causes a display to display the fluid information.

11 Claims, 10 Drawing Sheets

(51) Int. Cl.
    *A61B 5/055*     (2006.01)
    *G06T 7/00*     (2017.01)
    *G06T 7/223*     (2017.01)

(56) References Cited

U.S. PATENT DOCUMENTS

| | | |
|---|---|---|
| 9,814,531 B2 | 11/2017 | Yagi et al. |
| 9,968,409 B2 | 5/2018 | Yagi et al. |
| 2015/0127031 A1 | 5/2015 | Yagi et al. |

FOREIGN PATENT DOCUMENTS

| | | |
|---|---|---|
| JP | 2006000421 | 1/2006 |
| JP | 2017113578 | 6/2017 |

OTHER PUBLICATIONS

Stalder, Aurélien F., et al. "Quantitative 2D and 3D phase contrast MRI: optimized analysis of blood flow and vessel wall parameters." Magnetic Resonance in Medicine: An Official Journal of the International Society for Magnetic Resonance in Medicine 60.5 (2008): 1218-1231.*

Zhou, Yue, Chunhian Lee, and Jingying Wang. "The computational fluid dynamics analyses on hemodynamic characteristics in stenosed arterial models." Journal of Healthcare Engineering 2018 (2018).*

"International Search Report (Form PCT/ISA/210) of PCT/JP2020/042058," mailed on Feb. 2, 2021, with English translation thereof, pp. 1-5.

"Written Opinion of the International Searching Authority (Form PCT/ISA/237)" of PCT/JP2020/042058, mailed on Feb. 2, 2021, with English translation thereof, pp. 1-10.

"Office Action of Japan Counterpart Application", issued on May 16, 2023, with English translation thereof, p. 1-p. 8.

* cited by examiner

FIG. 5

| SIZE (mm) | SAMPLING INTERVAL (PIXELS) |
|---|---|
| 0 TO 10 | 2 |
| 10 TO 15 | 4 |
| 15 TO 20 | 6 |
| 20 TO 25 | 8 |
| 25 TO 30 | 10 |
| 30 TO 35 | 12 |

~LUT1

FLUID ANALYSIS APPARATUS, FLUID ANALYSIS METHOD, AND FLUID ANALYSIS PROGRAM

CROSS-REFERENCE TO RELATED APPLICATIONS

This application is a Continuation of PCT International Application No. PCT/JP2020/042058 filed on Nov. 11, 2020, which claims priority under 35 U.S.C § 119(a) to Japanese Patent Application No. 2019-235138 filed on Dec. 25, 2019. Each of the above application(s) is hereby expressly incorporated by reference, in its entirety, into the present application.

BACKGROUND OF THE INVENTION

1. Field of the Invention

The present disclosure relates to a fluid analysis apparatus, a fluid analysis method, and a fluid analysis program for analyzing and displaying flow of a fluid.

2. Description of the Related Art

In recent years, blood flow in blood vessels has been analyzed by using a medical image obtained by imaging a heart, a brain, or the like. As a blood flow analysis method using such a medical image, for example, a 4D flow method of measuring actual blood flow four-dimensionally has been used. In the 4D flow method, for example, by using a three-dimensional magnetic resonance imaging (MRI) image captured by three-dimensional cine phase contrast magnetic resonance imaging, a flow velocity vector is derived for each voxel, each pixel, or each region, and the flow velocity vectors are dynamically displayed along with the flow of time. A method for simulating blood flow by a blood flow analysis using computational fluid dynamics (CFD) has also been used.

In addition, a method has been proposed for displaying results of the above 4D flow and CFD analysis by, for example, streamlines, path lines, streak lines, or the like, to display the blood flow three-dimensionally.

To visualize the blood flow in a state close to the actual flow in blood vessels, a flow velocity vector may be displayed for each voxel of an MRI image. However, if the flow velocity vectors are drawn for all the voxels, the information amount becomes enormous, and drawing processing requires an enormous amount of time. In addition, if the flow velocity vectors are displayed for all the voxels, intervals between the flow velocity vectors become so dense that it is difficult to grasp the analysis results.

On the other hand, by increasing or decreasing sampling intervals for displaying the flow velocity vectors, the quantity of flow velocity vectors to be displayed can be increased or decreased. However, if the sampling intervals are fixed, it may be difficult to view the displayed flow velocity vectors because, for example, the flow velocity vectors may be drawn roughly in a portion to be focused on in blood vessels or, on the contrary, the flow velocity vectors may be drawn densely in a portion where not so much information is necessary.

Thus, various methods for setting the sampling intervals of the flow velocity vectors have been proposed. For example, JP1996-33625A (JP-H-8-33625A) proposes a method for setting the sampling intervals in accordance with a displayed body part, a display depth, the area of a region of interest, or the like, when displaying the flow velocity vectors on the basis of information on a blood flow velocity obtained from an ultrasound diagnostic apparatus. In addition, JP2006-000421A proposes a method for displaying the flow velocity vectors at an appropriate density by thinning out the flow velocity vectors when displaying the flow velocity vectors on the basis of information on a blood flow velocity obtained from an ultrasound diagnostic apparatus.

SUMMARY OF THE INVENTION

However, if the sampling intervals of the flow velocity vectors are set in accordance with the displayed body part or display depth as in the method described in JP1996-33625A (JP-H-8-33625A), the flow velocity vectors may be drawn roughly in a portion to be focused on in blood vessels or, on the contrary, the flow velocity vectors may be drawn densely in a portion where not so much information is necessary. In addition, by setting the sampling intervals in accordance with the area of a region of interest, a user needs to set the region of interest. Furthermore, although the flow velocity vectors are thinned out in the method described in JP2006-000421A, the reference for thinning out the flow velocity vectors is not clear.

The present disclosure has been made in view of the above circumstances, and an object thereof is to enable fluid information such as a flow velocity vector to be displayed at an appropriate sampling interval without imposing a load on a user.

A first fluid analysis apparatus according to the present disclosure includes at least one processor configured to:
analyze an image obtained by imaging a subject including a tubular structure in which a fluid flows, thereby deriving fluid information regarding flow of the fluid at each of pixel positions in the tubular structure;
set a sampling interval for displaying the fluid information in accordance with a size of a region intersecting a center line of the tubular structure included in the image; and
sample the fluid information at the set sampling interval and cause a display to display the fluid information.

A second fluid analysis apparatus according to the present disclosure includes at least one processor configured to:
set, in accordance with a size of a region intersecting a center line of a tubular structure in which a fluid flows, the tubular structure being included in an image obtained by imaging a subject including the tubular structure, a sampling interval for displaying fluid information regarding flow of the fluid at each of pixel positions in the tubular structure;
analyze the image, thereby deriving, at the set sampling interval, the fluid information regarding the flow of the fluid at each of pixel positions in the tubular structure; and
cause a display to display the fluid information.

Examples of "fluid information regarding flow of the fluid" include a flow velocity vector, a wall shear stress (WSS), a vorticity, and the like.

In the first and second fluid analysis apparatuses according to the present disclosure, the processor may be configured to decrease the sampling interval as the size is smaller.

In the first and second fluid analysis apparatuses according to the present disclosure, the processor may be configured to set the sampling interval in a direction intersecting the center line of the tubular structure.

In the first and second fluid analysis apparatuses according to the present disclosure, the processor may be configured to set the sampling interval in a direction in which the center line of the tubular structure extends.

In the first and second fluid analysis apparatuses according to the present disclosure, the processor may be configured to cause the display to display the fluid information as a vector.

In the first and second fluid analysis apparatuses according to the present disclosure, the processor may be configured to thicken a width of the vector as the sampling interval is larger.

In the first and second fluid analysis apparatuses according to the present disclosure, the image may be a three-dimensional image obtained by imaging the subject by three-dimensional cine phase contrast magnetic resonance imaging, and the processor may be configured to derive, as the fluid information, a flow velocity vector of the fluid obtained by analyzing the three-dimensional image.

In the first and second fluid analysis apparatuses according to the present disclosure, the processor may be configured to derive, as the fluid information, a flow velocity vector of the fluid obtained by simulating the flow of the fluid by an analysis using computational fluid dynamics.

In the first and second fluid analysis apparatuses according to the present disclosure, the tubular structure may be a blood vessel, and the fluid may be blood.

In a first fluid analysis method according to the present disclosure, an image obtained by imaging a subject including a tubular structure in which a fluid flows is analyzed, thereby deriving fluid information regarding flow of the fluid at each of pixel positions in the tubular structure;

a sampling interval for displaying the fluid information is set in accordance with a size of a region intersecting a center line of the tubular structure included in the image; and the fluid information is sampled at the set sampling interval and a display is caused to display the fluid information.

In a second fluid analysis method according to the present disclosure, in accordance with a size of a region intersecting a center line of a tubular structure in which a fluid flows, the tubular structure being included in an image obtained by imaging a subject including the tubular structure, a sampling interval for displaying fluid information regarding flow of the fluid at each of pixel positions in the tubular structure is set;

the image is analyzed, thereby deriving, at the set sampling interval, the fluid information regarding the flow of the fluid at each of pixel positions in the tubular structure; and a display is caused to display the fluid information.

Note that a program for causing a computer to execute the first and second fluid analysis methods according to the present disclosure may also be provided.

According to the present disclosure, the fluid information can be displayed at an appropriate sampling interval without imposing a load on a user.

BRIEF DESCRIPTION OF THE DRAWINGS

FIG. 5 is a diagram illustrating a table in which a size of a cross section and the sampling interval are associated with each other;

DESCRIPTION OF THE PREFERRED EMBODIMENTS

Figure 1:
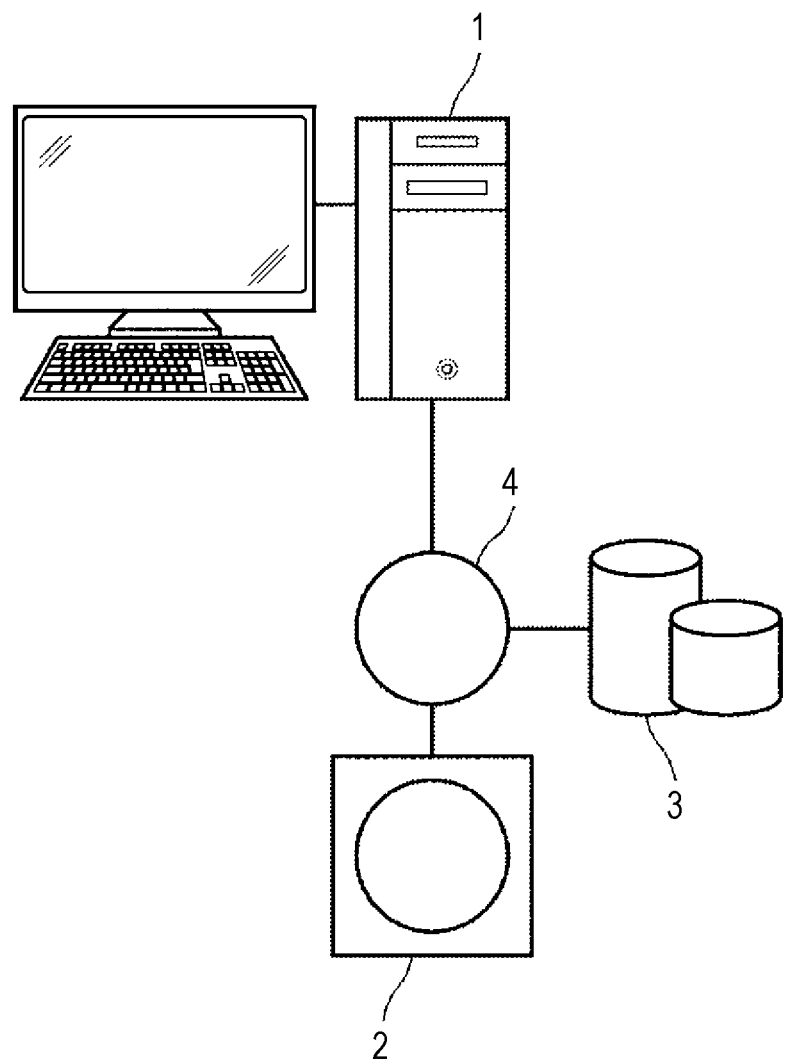
FIG. 1 is a hardware configuration diagram illustrating an overall diagnosis support system to which a fluid analysis apparatus according to a first embodiment of the present disclosure is applied.

Now, embodiments of the present disclosure will be described with reference to the drawings. FIG. 1 is a hardware configuration diagram illustrating an overall diagnosis support system to which a fluid analysis apparatus according to a first embodiment of the present disclosure is applied. As illustrated in FIG. 1, in the diagnosis support system, a fluid analysis apparatus 1 according to this embodiment, a three-dimensional imaging apparatus 2, and an image storage server 3 are communicably connected via a network 4.

The three-dimensional imaging apparatus 2 is an apparatus that images a diagnosis-target body part of a subject thereby generating a three-dimensional image representing the body part. Specifically, the three-dimensional imaging apparatus 2 is a CT apparatus, an MM apparatus, a positron emission tomography (PET) apparatus, or the like. A three-dimensional image generated by the three-dimensional imaging apparatus 2 is transmitted to the image storage server 3 and is stored therein. Although this embodiment describes a case of acquiring a three-dimensional image of the aorta of a patient, the present disclosure is not limited to this, and the three-dimensional image may be an image of another blood vessel. In addition, in this embodiment, the three-dimensional imaging apparatus 2 is an MM apparatus, and an MM image obtained by imaging a subject by three-dimensional cine phase contrast magnetic resonance imaging in the MRI apparatus is acquired as a three-dimensional image G0. However, the type of the three-dimensional image to be acquired is not limited to this. In addition, the aorta corresponds to a tubular structure in the present disclosure, and blood corresponds to a fluid in the present disclosure.

The image storage server 3 is a computer that stores and manages various types of data and includes an external mass storage device and database management software. The image storage server 3 communicates with the other apparatuses via the network 4 by wire or wirelessly to transmit and receive image data or the like. Specifically, the image storage server 3 acquires various types of data including image data of a three-dimensional image generated by the three-dimensional imaging apparatus 2 via the network and stores the image data in a recording medium such as the external mass storage device to manage the image data. Note that the form of storage of image data and communication between the apparatuses via the network 4 conform to a protocol such as Digital Imaging and Communication in Medicine (DICOM).

The fluid analysis apparatus 1 is a single computer in which a fluid analysis program according to the present disclosure is installed. The computer may be a workstation or a personal computer that a physician who performs diagnosis directly operates, or may be a server computer connected to the work station or personal computer via the network. The fluid analysis program is stored in a storage device of the server computer connected to the network or a network storage in an externally accessible state, is downloaded to a computer used by a physician on demand, and is installed. Alternatively, the fluid analysis program is recorded on a recording medium such as a digital versatile disc (DVD) or a compact disc read only memory (CD-ROM), is distributed, and is installed in a computer from the recording medium.

Figure 2:
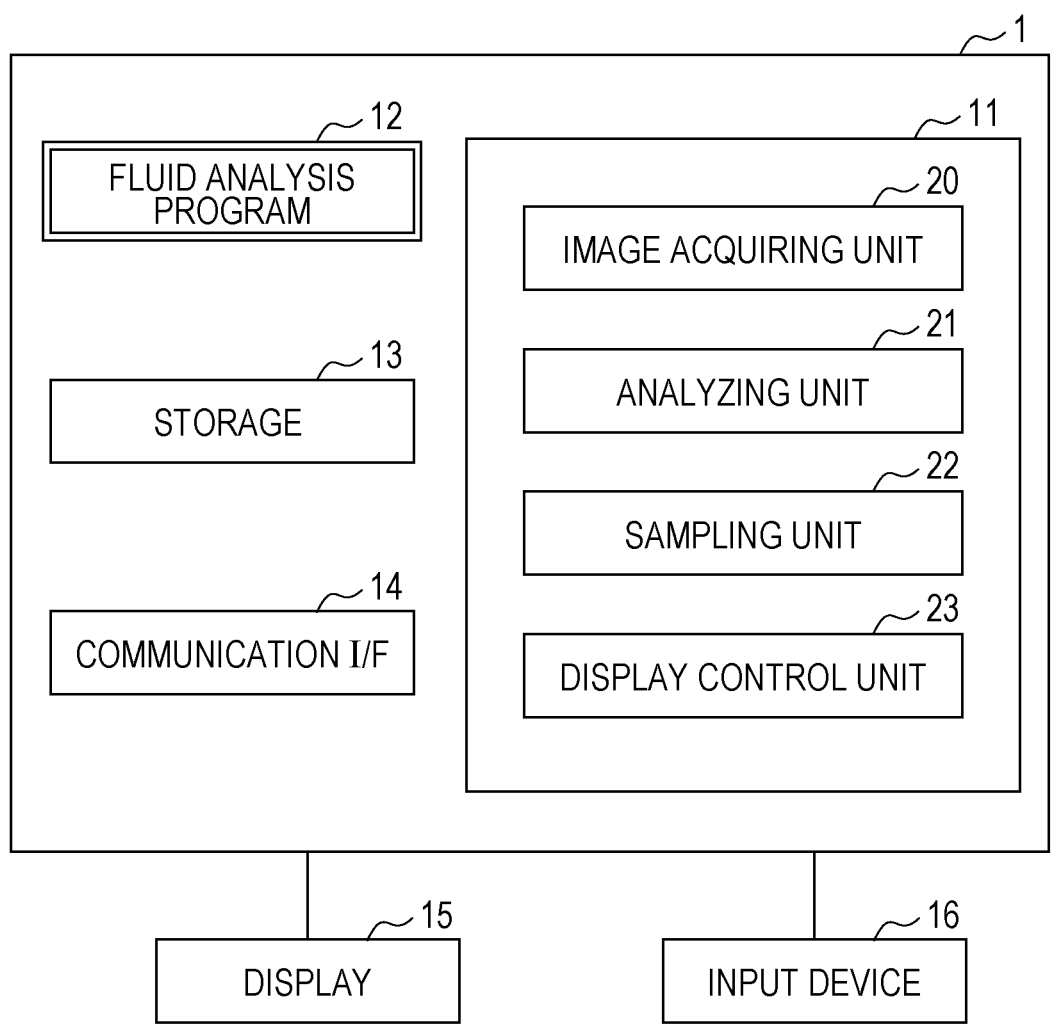
FIG. 2 is a diagram illustrating a schematic configuration of the fluid analysis apparatus according to the first embodiment of the present disclosure.

FIG. 2 is a diagram illustrating a schematic configuration of the fluid analysis apparatus implemented by the fluid analysis program being installed in a computer. As illustrated in FIG. 2, the fluid analysis apparatus 1 includes a central processing unit (CPU) 11, a memory 12, a storage 13, and a communication interface (I/F) 14 as a configuration of a standard workstation. In addition, a display 15 such as a liquid crystal display and an input device 16 including a keyboard and a mouse are connected to the fluid analysis apparatus 1. The CPU 11 corresponds to a processor.

The storage 13 is constituted by a storage device such as a hard disk drive or a solid state drive (SSD) and stores various types of information including a three-dimensional image acquired from the image storage server 3 via the network 4 and information necessary for processing.

The communication I/F 14 is a network interface for controlling transmission of various types of information between the fluid analysis apparatus 1 and an external apparatus such as the image storage server 3 via the network 4.

The memory 12 stores a fluid analysis program according to the first embodiment. As processes to be executed by the CPU 11, the fluid analysis program prescribes an image acquiring process for acquiring the three-dimensional image G0 obtained by the three-dimensional imaging apparatus 2 imaging a subject; an analyzing process for analyzing the three-dimensional image G0 and deriving fluid information regarding blood flow at each of pixel positions in the aorta; a sampling process for setting a sampling interval for displaying the fluid information in accordance with the size of a region intersecting the center line of the aorta included in the three-dimensional image G0; and a display control process for sampling the fluid information at the set sampling interval and displaying the fluid information on the display 15.

By the CPU 11 executing these processes in accordance with the program, the computer functions as an image acquiring unit 20, an analyzing unit 21, a sampling unit 22, and a display control unit 23.

The image acquiring unit 20 acquires the three-dimensional image G0 from the image storage server 3. Note that, if the three-dimensional image G0 is already stored in the storage 13, the image acquiring unit 20 may acquire the three-dimensional image G0 from the storage 13.

The analyzing unit 21 analyzes the three-dimensional image G0 and derives fluid information R0 regarding blood flow at each of pixel positions in the aorta. In this embodiment, the analyzing unit 21 first extracts a blood vessel region from the three-dimensional image G0. Specifically, the analyzing unit 21 performs a multiresolution analysis on the three-dimensional image G0, performs an eigenvalue analysis of the Hessian matrix on images with different resolutions, and integrating the analysis results of the images with different resolutions, thereby extracting, as the blood vessel region, a region of the aortic arch as an aggregate of linear structures (blood vessels) with various sizes in a heart region included in the three-dimensional image G0 (for example, see Y Sato, et al., "Three-dimensional multi-scale line filter for segmentation and visualization of curvilinear structures in medical images", Medical Image Analysis, June 1998, Vol. 2, No. 2, p.p. 143-168). Furthermore, the analyzing unit 21 may couple center points of the extracted linear structures by using a minimum spanning tree algorithm or the like to generate tree-structure data representing the aorta, and then, may obtain a cross section orthogonal to a core wire at each point (node of tree-structure data) on the core wire obtained by connecting the center points of the extracted aorta, recognize the outline of the aorta by using a known segmentation method such as graph cuts on each cross section, and associate information representing the outline to a corresponding node of the tree-structure data, thereby extracting a region of the aorta as the blood vessel region.

Note that the method for extracting the blood vessel region is not limited to the above method, and another known method such as region expansion may also be used.

Subsequently, the analyzing unit 21 derives a flow velocity vector at each voxel position in the blood vessels as the fluid information R0 by using velocity information in the blood vessel region extracted from the three-dimensional image G0.

Figure 3:
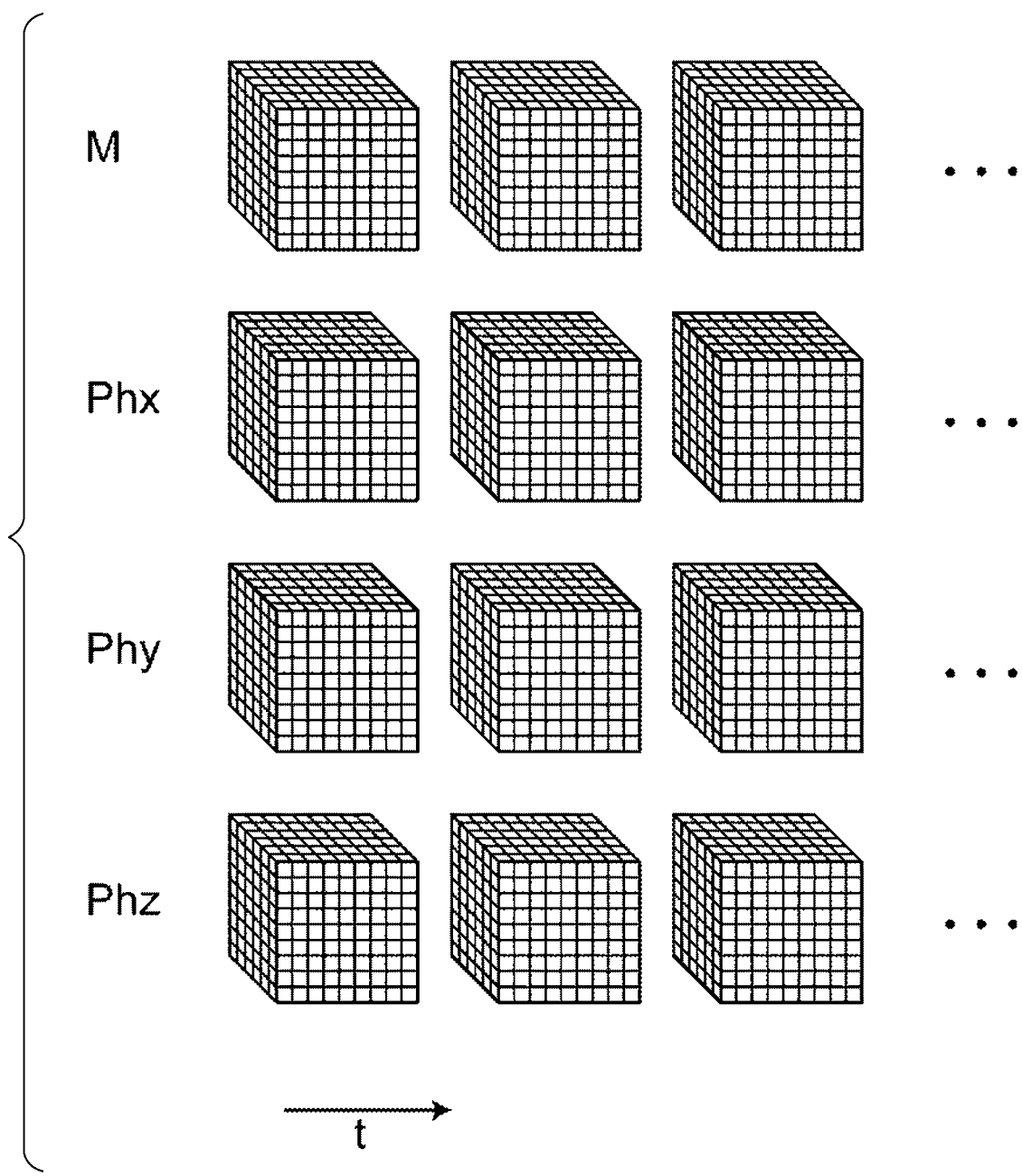
FIG. 3 is a diagram illustrating a three-dimensional image captured by three-dimensional cine phase contrast magnetic resonance imaging.

FIG. 3 is a diagram illustrating the three-dimensional image G0 captured by three-dimensional cine phase contrast magnetic resonance imaging. As illustrated in FIG. 3, image data of the three-dimensional image G0 captured by three-dimensional cine phase contrast magnetic resonance imaging includes three-dimensional data of magnitude data M, X-axis-direction phase data Phx, Y-axis-direction phase data Phy, and Z-axis-direction phase data Phz obtained in a predetermined cycle (e.g., cardiac cycle) along time t. The X-axis-direction phase data Phx, the Y-axis-direction phase data Phy, and the Z-axis-direction phase data Phz are generated by encoding (velocity encoding: VENC) the magnitude data M in the X-axis direction, the Y-axis direction, and the Z-axis direction. The X-axis-direction phase data Phx, the Y-axis-direction phase data Phy, and the Z-axis-direction phase data Phz are data representing the flow velocity in the respective axis directions. From the three kinds of phase data, the analyzing unit 21 derives a three-dimensional flow velocity vector (hereinafter referred to as flow velocity vector) at each voxel position of the three-dimensional image G0 as the fluid information R0.

Note that the image acquiring unit 20 may acquire three-dimensional ultrasound images obtained in a time-series manner by Doppler measurement and may acquire flow velocity vectors by using the velocity information in the blood vessel region obtained on the basis of the ultrasound images to derive the fluid information R0.

The sampling unit 22 sets a sampling interval for displaying the fluid information R0 in accordance with the size of a region intersecting the center line of the aorta included in the three-dimensional image G0. In this embodiment, the analyzing unit 21 sets the sampling interval for displaying the fluid information R0 in accordance with the size of the region intersecting the center line using, as the center line, a core line derived when the blood vessel region is extracted.

Figure 4:
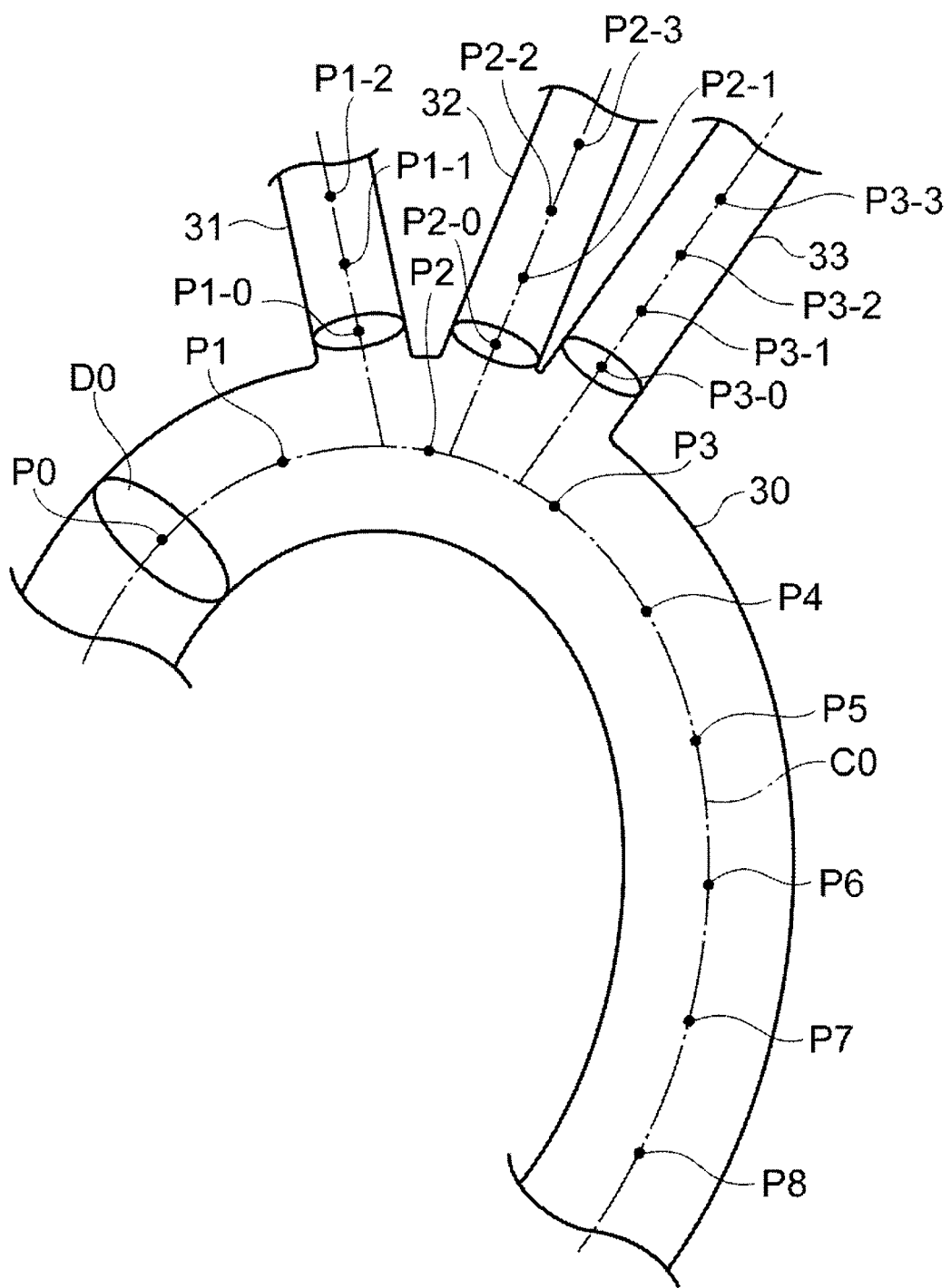
FIG. 4 is a diagram for describing setting of a sampling interval.

FIG. 4 is a diagram for describing setting of the sampling interval. Note that FIG. 4 illustrates an aortic arch 30, a brachiocephalic artery 31, a left common carotid artery 32, and a left subclavian artery 33 in the extracted aorta. As illustrated in FIG. 4, the sampling unit 22 first sets a cross section D0 intersecting a center line C0 of the aortic arch 30 at a predetermined initial reference position P0. Specifically, the sampling unit 22 defines the cross section D0 orthogonal to the center line C0. Note the initial reference position P0 may be set in the following manner. The display 15 displays a volume-rendering image or the like of the extracted aorta, and an operator designates the initial reference position P0 on the displayed image of the aorta by using the input device 16.

Subsequently, the sampling unit 22 derives the size of the cross section D0. As the size of the cross section D0, the diameter or radius of the cross section D0, the area of the cross section D0, or the volume of a predetermined thickness including the cross section D0 may be used. The thickness may be 1 mm, for example, but is not limited to this.

Subsequently, on the basis of the initial reference position P0, the sampling unit 22 sets each of a plurality of reference positions Pk (k=1 to n) for setting the sampling interval along the center line C0 at a predetermined interval. The predetermined interval may be any given interval, such as 5 mm, 1 cm, or 3 cm. Then, the size of a cross section Dk is derived at each of the reference positions Pk.

In a similar manner, the sampling unit 22 also sets initial reference positions P1-0, P2-0, and P3-0 for the brachiocephalic artery 31, the left common carotid artery 32, and the left subclavian artery 33, sets reference positions P1-1, P1-2 . . . , P2-1, P2-2 . . . , P3-1, P3-2 . . . at predetermined intervals, and derives the sizes of cross sections at the initial reference positions and the reference positions.

Subsequently, in accordance with the size of the cross section Dk, the sampling unit 22 sets the sampling interval for displaying the fluid information R0. Specifically, the smaller the cross section Dk is, the smaller the sampling interval is. In this embodiment, as illustrated in FIG. 5, a table LUT1 in which the size of the cross section Dk and the sampling interval are associated with each other is stored in the storage 13. Although the size of the cross section Dk is the diameter in FIG. 5, the size of the cross section Dk may also be the radius, the area, or the volume. In addition, "0 to 10" in FIG. 5 indicates that the diameter is greater than 0 mm and less than or equal to 10 mm. Furthermore, the numerical value of the sampling interval denotes the number of pixels that are present between pixels at which the fluid information R0 is to be displayed. Since the diameter of the aorta is about 35 mm at most, the table LUT1 illustrates the sizes up to 35 mm. As illustrated in FIG. 5, in the table LUT1, the size of the cross section Dk increments by 5 mm, while the sampling interval increments by 2 pixels. With reference to the table LUT1, the sampling unit 22 sets the sampling interval in accordance with the size of the cross section Dk. Note that the sampling interval is not limited to the values illustrated in the table LUT1.

Instead of setting the sampling interval with reference to the table LUT1, the sampling interval may be set in proportion to the size of the cross section Dk.

The sampling interval herein is a three-dimensional sampling interval in the three-dimensional image G0. However, a two-dimensional sampling interval may also be set on the assumption that a two-dimensional cross section in the aorta is displayed.

Figure 6:
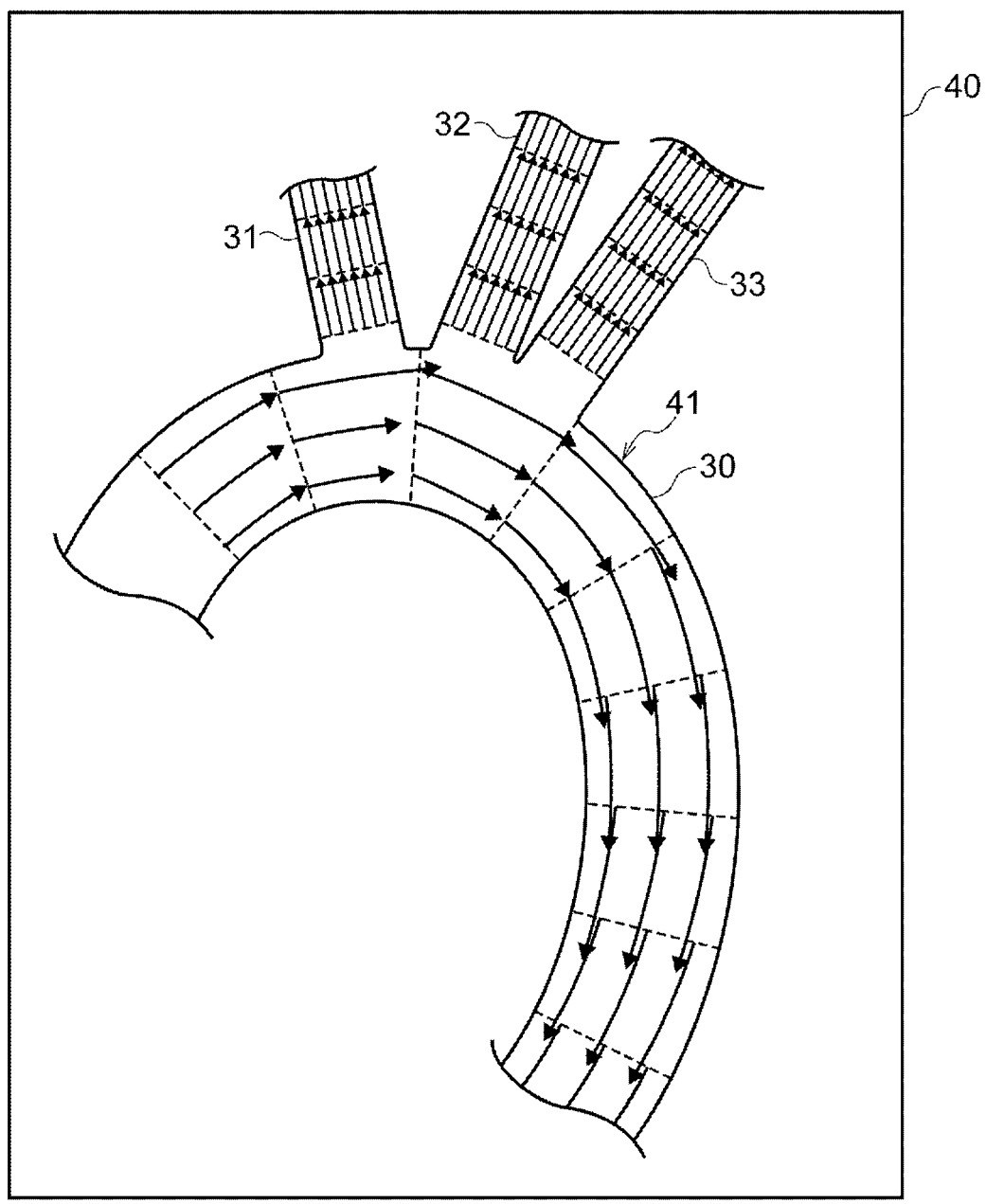
FIG. 6 is a diagram illustrating a display screen of fluid information.

The display control unit 23 samples the fluid information R0 at the sampling interval set by the sampling unit 22 and causes the display 15 to display the fluid information R0. FIG. 6 is a diagram illustrating a display screen of the fluid information R0 displayed on the display 15. As illustrated in FIG. 6, on a display screen 40, a region 41 of the aortic arch 30 including the brachiocephalic artery 31, the left common carotid artery 32, and the left subclavian artery 33 is displayed. From a cross section orthogonal to a reference position in FIG. 4 in the region 41 as a starting point, the fluid information R0 is sampled at the sampling interval set by the sampling unit 22 and displayed. Although FIG. 6 illustrates a two-dimensional image of the aortic arch 30 including the brachiocephalic artery 31, the left common carotid artery 32, and the left subclavian artery 33 for description, actually, the aortic arch 30 including the brachiocephalic artery 31, the left common carotid artery 32, and the left subclavian artery 33 is displayed three-dimensionally by a method such as volume rendering or the like.

As illustrated in FIG. 6, in the aortic arch 30, the sampling interval of the fluid information R0 is relatively large, while in the brachiocephalic artery 31, the left common carotid artery 32, and the left subclavian artery 33, which are thinner than the aortic arch 30, the sampling interval of the fluid information R0 is relatively small. Note that in FIG. 6, the sampling interval in the direction in which the center line C0 extends is an interval between reference positions.

Figure 7:
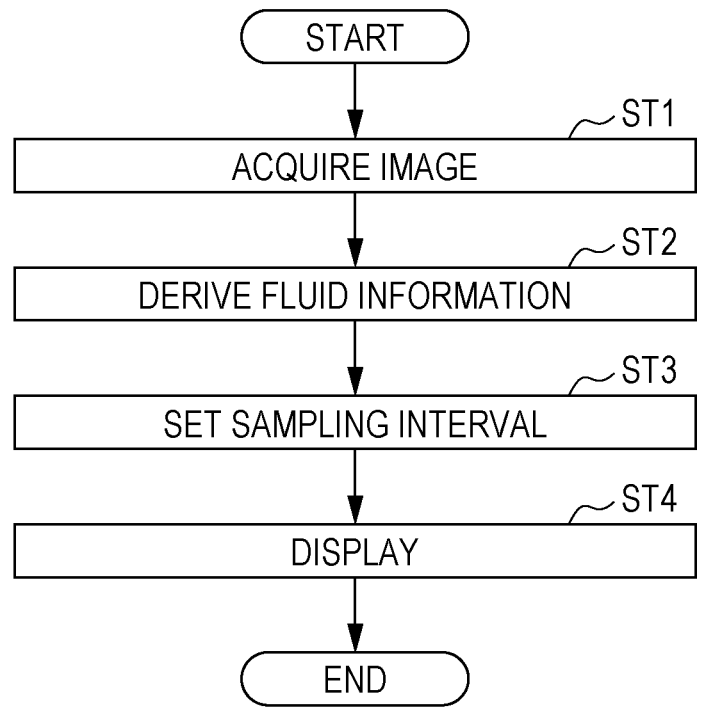
FIG. 7 is a flowchart illustrating a process performed in the first embodiment.

Next, a process performed in the first embodiment will be described. FIG. 7 is a flowchart illustrating the process performed in this embodiment. First, the image acquiring unit 20 acquires the three-dimensional image G0 from the image storage server 3 (acquire image; step ST1). Subsequently, the analyzing unit 21 analyzes the three-dimensional image G0 and derives the fluid information R0 regarding blood flow at each position in the blood vessels (step ST2). Subsequently, the sampling unit 22 sets the sampling interval for displaying the fluid information R0 in accordance with the size of the region intersecting the center line C0 of the aorta included in the three-dimensional image G0 (step ST3). Furthermore, the display control unit 23 samples the fluid information R0 at the set sampling interval and causes the display 15 to display the fluid information R0 (step ST4), and the process ends.

In the above manner, in the first embodiment, the sampling interval for displaying the fluid information R0 is set in accordance with the size of the cross section Dk intersecting the center line C0 of the aortic arch 30, and the fluid information R0 is sampled at the set sampling interval and displayed. Accordingly, the fluid information R0 can be displayed at an appropriate sampling interval without imposing a load on a user.

Although the fluid information R0 is displayed by using the predetermined interval between the reference positions as the sampling interval in the direction in which the center line C0 of the blood vessel extends in the above embodiment, the present disclosure is not limited to this. Also in the direction in which the center line C0 of the blood vessel extends, the sampling interval for displaying the fluid information R0 may be set in accordance with the size of the region intersecting the center line C0. Now, setting of the sampling interval in the direction in which the center line C0 extends will be described.

Figure 8:
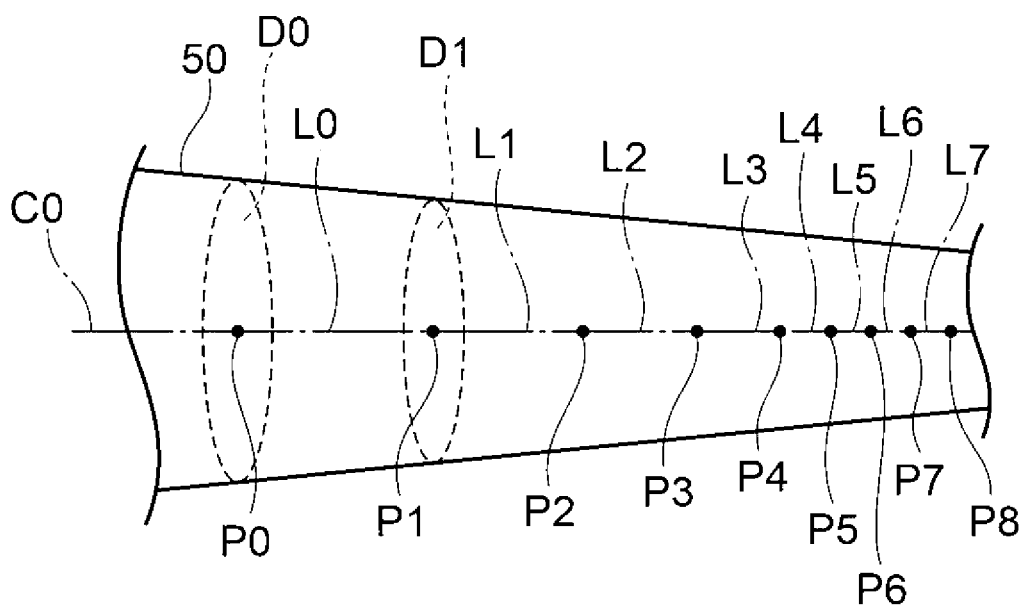
FIG. 8 is a diagram for describing setting of the sampling interval in a direction in which a center line extends.

FIG. 8 is a diagram for describing setting of the sampling interval in the direction in which the center line C0 extends. Note that FIG. 8 illustrates a blood vessel 50 whose diameter gradually decreases for the ease of description. In the blood vessel 50, the direction in which the diameter decreases is the downstream side of the blood flow. First, as illustrated in FIG. 8, on the basis of the initial reference position P0, the sampling unit 22 sets a next reference position P1 with a predetermined initial interval L0 interposed along the center line C0. The initial interval L0 is the sampling interval between the initial reference position P0 and the reference position P1. Note that the initial interval L0 may be any given interval, such as 5 mm, 1 cm, 3 cm, and the like.

Subsequently, the sampling unit 22 sets cross sections D0 and D1 at the initial reference position P0 and the reference position P1, respectively, and derives a ratio a1 of the size of the cross section D1 to the size of the cross section D0. The sampling unit 22 multiplies the initial interval L0 by the ratio a1, thereby determining an interval L1 between the reference position P1 and a next reference position P2. That is, the interval L1 is set according to $L1=a1 \times L0$. The interval L1 is the sampling interval between the reference position P1 and the reference position P2. Herein, since D1<D0, L1<L0 is satisfied.

Subsequently, the sampling unit 22 sets a cross section D2 (not illustrated) at the reference position P2 and derives a ratio a2 of the size of the cross section D2 to the size of the cross section D1. The sampling unit 22 multiplies the interval L1 by the ratio a2, thereby determining an interval L2 between the reference position P2 and a next reference position P3. That is, the interval L2 is set according to $L2=a2 \times L1$. The interval L2 is the sampling interval between the reference position P2 and the reference position P3. Herein, since D2<D1, L2<L1 is satisfied.

In a similar manner, the sampling unit 22 sets reference positions P3, P4, P5 . . . , thereby setting sampling intervals L3, L4, L5 . . . in the direction in which the center line C0 extends in the blood vessel 50. Thus, as illustrated in FIG. 8, as the blood vessel 50 becomes thinner, that is, as the region intersecting the center line C0 becomes smaller, the sampling interval in the direction in which the center line C0 extends becomes smaller. That is, the relationship between the initial interval L0 and the sampling intervals L1 to L5 is L5<L4<L3<L2<L1<L0.

If the sampling interval in the direction in which the center line C0 extends becomes too small, the displayed fluid information R0 is difficult to view. Thus, if the sampling interval becomes less than or equal to a predetermined threshold, the sampling interval in the direction in which the center line C0 extends may be fixed. In FIG. 8, sampling intervals L5 to L7 are fixed.

On the other hand, also in a case where the sampling interval is set in the direction in which the center line C0 extends as in the above embodiment, in the direction intersecting the center line C0, the sampling interval may be set in accordance with the size of the region intersecting the center line C0. Note that the sampling interval may be set only in the direction in which the center line C0 extends, and a predetermined sampling interval may be set in the direction intersecting the center line C0.

Figure 9:
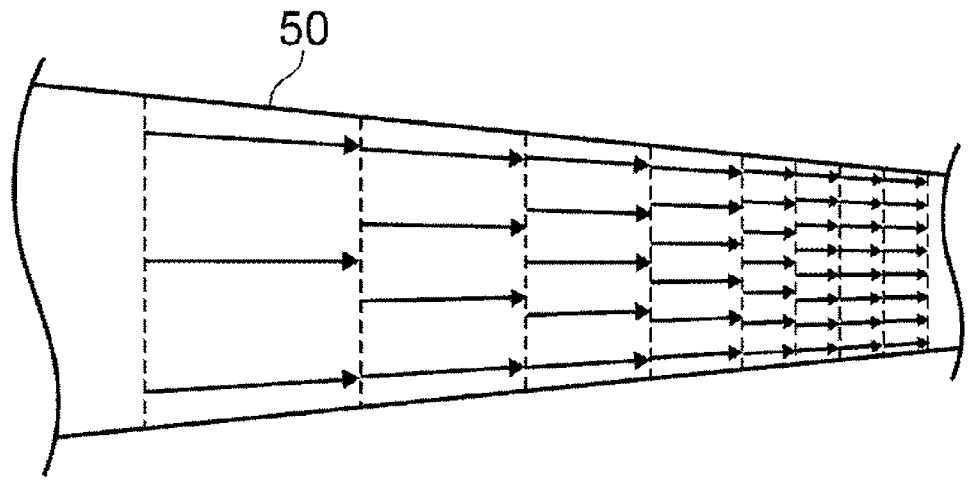
FIG. 9 is a diagram illustrating a display screen of fluid information.

FIG. 9 is a diagram illustrating a display screen of fluid information in a case where the sampling interval is set in both the direction in which the center line of the blood vessel extends and the direction intersecting the center line. Note that the positions of the broken lines illustrated in FIG. 9 correspond to the initial reference position P0 and reference positions P1 to P8 illustrated in FIG. 8. As illustrated in FIG. 9, as the diameter of the blood vessel 50 becomes smaller, the sampling interval of the fluid information R0 becomes smaller in both the direction in which the center line C0 extends and the direction intersecting the center line C0.

Although the analyzing unit 21 derives the fluid information R0 at each voxel position of the three-dimensional image G0 in the above first embodiment, the present disclosure is not limited to this. Before deriving the fluid information R0, the sampling unit 22 may set the sampling interval of the fluid information R0, and the analyzing unit 21 may derive the fluid information R0 at the set sampling interval. This will be described as a second embodiment below. Note that the configuration of the fluid analysis apparatus according to the second embodiment is the same as the configuration of the fluid analysis apparatus according to the first embodiment illustrated in FIG. 2, and only the process to be performed is different. Therefore, detailed description of the apparatus will be omitted below.

Figure 10:
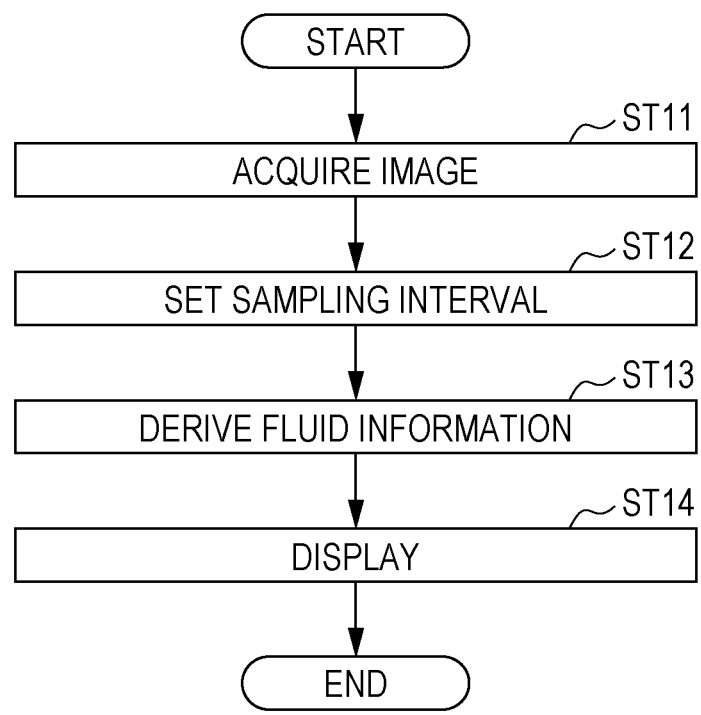
FIG. 10 is a flowchart illustrating a process performed in a second embodiment.

FIG. 10 is a flowchart illustrating the process performed in the second embodiment. First, the image acquiring unit 20 acquires the three-dimensional image G0 from the image storage server 3 (acquire image; step ST11). Subsequently, the sampling unit 22 sets the sampling interval for displaying the fluid information R0 in accordance with the size of the region intersecting the center line C0 of the aorta included in the three-dimensional image G0 (step ST12). Subsequently, the analyzing unit 21 analyzes the three-dimensional image G0 and derives the fluid information R0 regarding blood flow at each position in the blood vessels at the sampling interval set by the sampling unit 22 (step ST13). Furthermore, the display control unit 23 causes the display 15 to display the derived fluid information R0 (step ST14), and the process ends.

Figure 11:
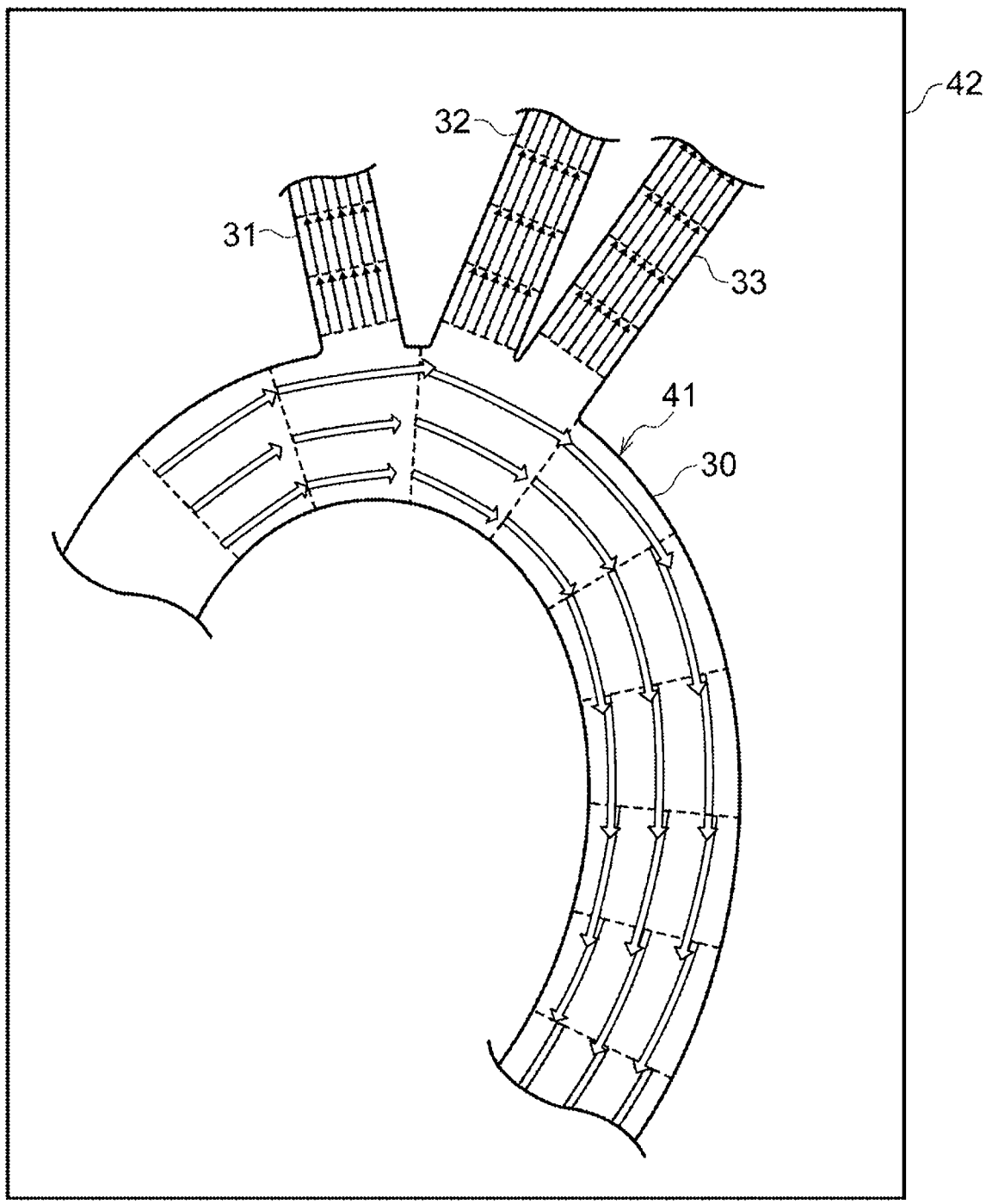
FIG. 11 is a diagram illustrating a display screen of fluid information.

Since the sampling interval is smaller as the diameter of the blood vessel is smaller in each of the above embodiments, in a blood vessel whose diameter is comparatively large, the fluid information R0 to be displayed becomes sparse. In this case, even if the blood flow is fast, the blood flow may appear slow on the display screen. Accordingly, in a blood vessel whose diameter is greater than or equal to a predetermined threshold, the line width of the fluid information R0 to be displayed may be thickened. FIG. 11 is a diagram illustrating a display screen on which the line width of the fluid information R0 to be displayed is thickened in a blood vessel whose diameter is greater than or equal to the predetermined threshold. As illustrated in FIG. 11, the line width of the fluid information R0 to be displayed in the aortic arch 30 is thickened on a display screen 42.

In addition, in each of the above embodiments, an MRI image obtained by imaging a subject by three-dimensional cine phase contrast magnetic resonance imaging is acquired as the three-dimensional image G0, and the fluid information R0 is derived by using the three-dimensional image G0. However, the present disclosure is not limited to this. A contrast CT image obtained by imaging a subject by using a contrast medium in a CT apparatus may be acquired as the three-dimensional image G0, and the analyzing unit 21 may analyze the blood flow by computational fluid dynamics (CFD), thereby deriving a flow velocity vector at each voxel position of the three-dimensional image G0 as the fluid information R0.

Figure 12:
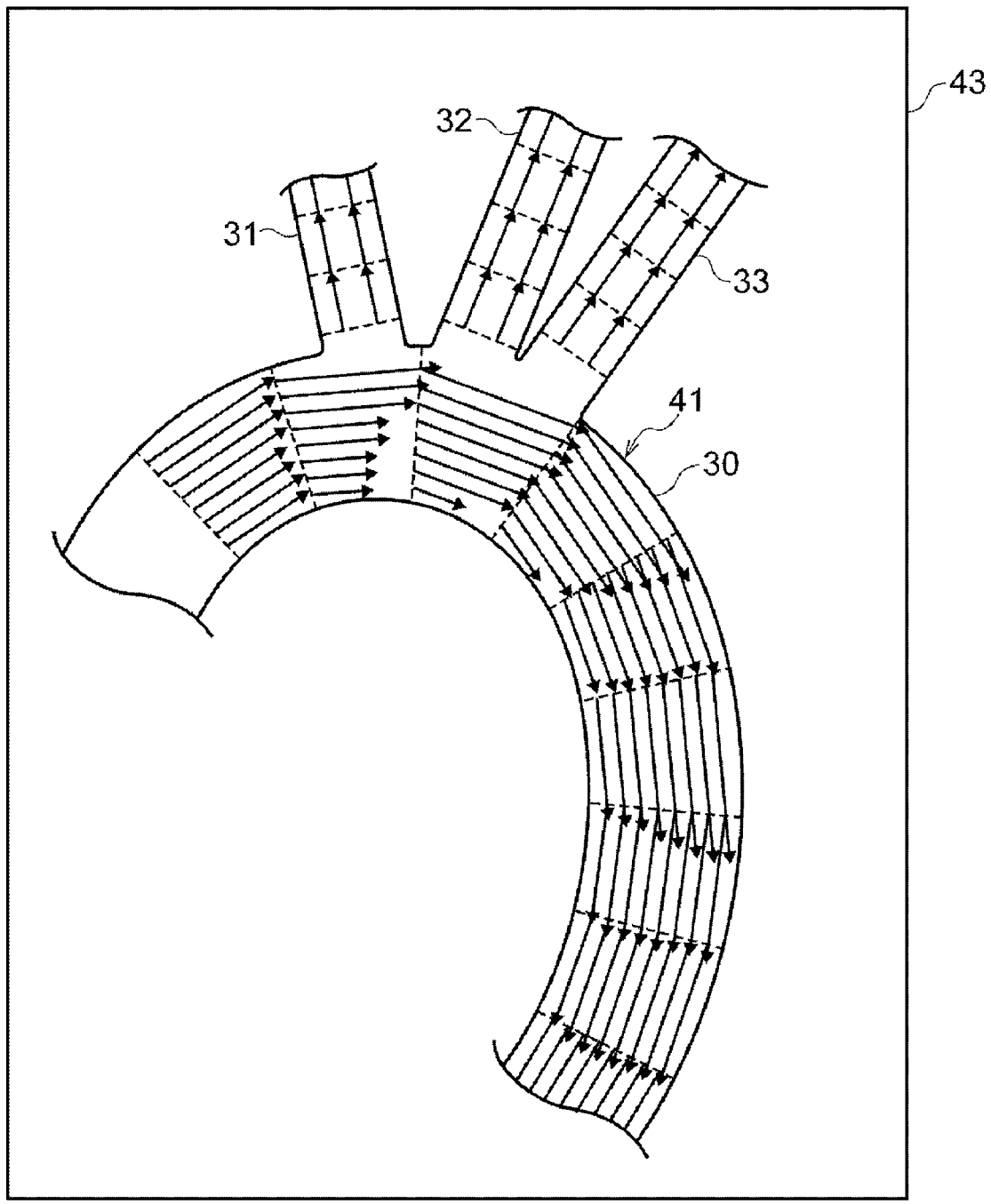
FIG. 12 is a diagram illustrating a display screen of fluid information.

Furthermore, in each of the above embodiments, the sampling interval for displaying the fluid information R0 is smaller as the cross section intersecting the center line C0 in the blood vessel such as the aorta is smaller. However, the present disclosure is not limited to this. As illustrated in a display screen 43 in FIG. 12, the sampling interval for displaying the fluid information R0 may be larger as the cross section intersecting the center line C0 in the blood vessel such as the aorta is smaller.

Furthermore, in each of the above embodiments, the flow velocity vector at each position in the blood vessel is derived as the fluid information R0. However, the present disclosure is not limited to this. In addition to the flow velocity vector, for example, a wall shear stress (WSS), a vorticity, or the like may also be used as the fluid information R0.

Furthermore, in each of the above embodiments, a blood vessel is used as a structure in which a fluid flows. However, the present disclosure is not limited to this. For example, in a case where the flow of cerebrospinal fluid is to be visualized, a ventricle of the brain in the cranium, in particular, a subarachnoid space, or a spinal subarachnoid space in a spinal canal, may also be used as the structure in which a fluid flows. In addition, a lymphatic vessel in which lymph flows may also be used.

Furthermore, in each of the above embodiments, an image targeting a human body is used. However, the present disclosure is not limited to this. For example, it is needless to say that the technique according to the present disclosure is applicable to a case where the flow of a fluid flowing in a pipe is analyzed.

In addition, in each of the above embodiments, for example, as a hardware configuration of a processing unit that executes various processes, such as the image acquiring unit 20, the analyzing unit 21, the sampling unit 22, and the display control unit 23, any of the following various processors below can be used. The various processors include, as described above, a CPU, which is a general-purpose processor that functions as various processing units by executing software (programs), and in addition, a programmable logic device (PLD), which is a processor in which the circuit configuration is changeable after manufacture, such as an FPGA (Field Programmable Gate Array), a dedicated electric circuit, which is a processor having a circuit configuration that is specially designed to execute specific processing, such as an ASIC (Application Specific Integrated Circuit), and the like.

One processing unit may be constituted by one of these various processors or may be constituted by two or more processors of the same type or different types in combination (e.g., a combination of a plurality of FPGAs or a combination of a CPU and an FPGA). In addition, a plurality of processing units may be constituted by one processor.

As a first example for constituting a plurality of processing units by one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one IC (Integrated Circuit) chip, as typified by a system on chip (SoC) or the like. In this manner, various processing units are constituted by one or more of the above various processors in terms of hardware configuration.

More specifically, the hardware configuration of these various processors may be electric circuitry constituted by combining circuit elements such as semiconductor elements.

REFERENCE SIGNS LIST 1 fluid analysis apparatus
2 three-dimensional imaging apparatus
3 image storage server
4 network
11 CPU
12 memory
13 storage
14 communication I/F
15 display
16 input device
20 image acquiring unit
21 analyzing unit
22 sampling unit
23 display control unit
30 aortic arch
31 brachiocephalic artery
32 left common carotid artery
33 left subclavian artery
40, 42, 43 display screen
41 region
50 blood vessel
C0 center line
D0 cross section
LUT 1 table
M magnitude data
Phx phase data
Phy phase data
Phz phase data
P0, P1-0, P2-0, P3-0 initial reference position
P1 to P8, P1-1, P1-2, P2-1, P2-2, P2-3, P3-1, P3-2, P3-3 reference position

What is claimed is:

1. A fluid analysis apparatus comprising
at least one processor configured to:
analyze an image obtained by imaging a subject including a tubular structure in which a fluid flows, thereby deriving fluid information regarding flow of the fluid at each of pixel positions in the tubular structure;
set a sampling interval for displaying the fluid information;
sample the fluid information at the set sampling interval and cause a display to display the fluid information as a vector; and
thicken a width of the vector as the sampling interval is larger,
wherein the sampling interval is set in a direction in which a center line of the tubular structure included in the image extends such that, in a direction intersecting the center line, the sampling interval is set in accordance with a size of a region intersecting the center line.

2. The fluid analysis apparatus according to claim 1, wherein the processor is configured to decrease the sampling interval as the size is smaller.

3. The fluid analysis apparatus according to claim 1, wherein
the image is a three-dimensional image obtained by imaging the subject by three-dimensional cine phase contrast magnetic resonance imaging, and
the processor is configured to derive, as the fluid information, a flow velocity vector of the fluid obtained by analyzing the three-dimensional image.

4. The fluid analysis apparatus according to claim 1, wherein the processor is configured to derive, as the fluid information, a flow velocity vector of the fluid obtained using computational fluid dynamics.

5. The fluid analysis apparatus according to claim 1, wherein the tubular structure is a blood vessel, and the fluid is blood.

6. A fluid analysis method comprising:
analyzing an image obtained by imaging a subject including a tubular structure in which a fluid flows, thereby deriving fluid information regarding flow of the fluid at each of pixel positions in the tubular structure;
setting a sampling interval for displaying the fluid information;

sampling the fluid information at the set sampling interval and causing a display to display the fluid information as a vector; and thickening a width of the vector as the sampling interval is larger, wherein the sampling interval is set in a direction in which a center line of the tubular structure included in the image extends such that, in a direction intersecting the center line, the sampling interval is set in accordance with a size of a region intersecting the center line.

7. A fluid analysis method comprising:

setting a sampling interval for displaying fluid information regarding flow of a fluid at each of pixel positions in a tubular structure in an image obtained by imaging a subject including the tubular structure in which the fluid flows;

analyzing the image, thereby deriving, at the set sampling interval, the fluid information regarding the flow of the fluid at each of pixel positions in the tubular structure;

causing a display to display the fluid information as a vector; and thickening a width of the vector as the sampling interval is larger, wherein the sampling interval is set in a direction in which a center line of the tubular structure included in the image extends such that, in a direction intersecting the center line, the sampling interval is set in accordance with a size of a region intersecting the center line.

8. A non-transitory computer readable recording medium storing a fluid analysis program for causing a computer to execute:

a procedure of analyzing an image obtained by imaging a subject including a tubular structure in which a fluid flows, thereby deriving fluid information regarding flow of the fluid at each of pixel positions in the tubular structure;

a procedure of setting a sampling interval for displaying the fluid information;

a procedure of sampling the fluid information at the set sampling interval and causing a display to display the fluid information as a vector; and a procedure of thickening a width of the vector as the sampling interval is larger, wherein the sampling interval is set in a direction in which a center line of the tubular structure included in the image extends such that, in a direction intersecting the center line, the sampling interval is set in accordance with a size of a region intersecting the center line.

9. A non-transitory computer readable recording medium storing a fluid analysis program for causing a computer to execute:

a procedure of setting a sampling interval for displaying fluid information regarding flow of a fluid at each of pixel positions in a tubular structure in an image obtained by imaging a subject including the tubular structure in which the fluid flows;

a procedure of analyzing the image, thereby deriving, at the set sampling interval, the fluid information regarding the flow of the fluid at each of pixel positions in the tubular structure;

a procedure of causing a display to display the fluid information as a vector; and a procedure of thickening a width of the vector as the sampling interval is larger, wherein the sampling interval is set in a direction in which a center line of the tubular structure included in the image extends such that, in a direction intersecting the center line, the sampling interval is set in accordance with a size of a region intersecting the center line.

10. A fluid analysis apparatus comprising at least one processor configured to:

set a sampling interval for displaying fluid information regarding flow of a fluid at each of pixel positions in a tubular structure in an image obtained by imaging a subject including the tubular structure in which the fluid flows;

analyze the image, thereby deriving, at the set sampling interval, the fluid information regarding the flow of the fluid at each of pixel positions in the tubular structure;

cause a display to display the fluid information as a vector; and thicken a width of the vector as the sampling interval is larger, wherein the sampling interval is set in a direction in which a center line of the tubular structure included in the image extends such that, in a direction intersecting the center line, the sampling interval is set in accordance with a size of a region intersecting the center line.

11. The fluid analysis apparatus according to claim 10, wherein the processor is configured to decrease the sampling interval as the size is smaller.

* * * * *